(12) United States Patent
Wang et al.

(10) Patent No.: US 10,188,424 B2
(45) Date of Patent: Jan. 29, 2019

(54) TROCAR SET (71) Applicants: MEGAFORCE COMPANY LIMITED, New Taipei (TW); COREBIO TECHNOLOGIES CO., LTD., Taoyuan (TW)

(72) Inventors: Kai-Ping Wang, New Taipei (TW); Tien-Fu Chen, New Taipei (TW); Cheng-Ching Hsia, New Taipei (TW); Fen-Yuan Lin, New Taipei (TW); Fu-Po Wu, New Taipei (TW); Chih-Hao Chen, Taoyuan (TW)

(73) Assignees: MEGAFORCE COMPANY LIMITED, New Taipei (TW); COREBIO TECHNOLOGIES CO., LTD., Taoyuan (TW)

( * ) Notice: Subject to any disclaimer, the term of this patent is extended or adjusted under 35 U.S.C. 154(b) by 0 days.

(21) Appl. No.: 15/496,810

(22) Filed: Apr. 25, 2017

(65) Prior Publication Data
US 2018/0154091 A1    Jun. 7, 2018

(30) Foreign Application Priority Data
Dec. 1, 2016   (TW) .............................. 105139683 A (51) Int. Cl.
*A61B 17/34*    (2006.01)
*A61M 13/00*   (2006.01)
*A61B 17/02*    (2006.01)

(52) U.S. Cl.
CPC ...... *A61B 17/3423* (2013.01); *A61B 17/0218* (2013.01); *A61B 17/3421* (2013.01);
(Continued)

(58) Field of Classification Search
CPC .............. A61B 17/3417; A61B 17/348; A61B 2017/3484; A61B 2017/3419;
(Continued)

(56) References Cited

U.S. PATENT DOCUMENTS 3,856,020 A * 12/1974 Kovac ................... A61M 25/02
                                                       128/DIG. 26
5,591,194 A *  1/1997 Berthiaume .......... A61M 25/00
                                                       606/192
(Continued)

OTHER PUBLICATIONS

U.S. Appl. No. 15/496,831, filed Apr. 25, 2017.
U.S. Appl. No. 15/496,851, filed Apr. 25, 2017.

*Primary Examiner* — Andrew Gilbert
*Assistant Examiner* — John Doubrava
(74) *Attorney, Agent, or Firm* — Muncy, Geissler, Olds & Lowe, P.C.

(57) ABSTRACT

A trocar set includes a handle portion, a first sleeve, a second sleeve, and a gasbag. The handle portion includes a grip, a connection part, and a first gas valve. The connection part extends from the grip and includes an assembling channel. The first gas valve is connected to the connection part and communicates with the assembling channel. An assembling end of the first sleeve is assembled to the connection portion. A sleeving end of the first sleeve is provided with a first opening. The second sleeve is retractably connected to the sleeving end of the first sleeve. A sleeve wall of the second sleeve is provided with a second opening. The gasbag is connected to an end of the second sleeve away from the sleeving end and corresponds to the second opening. The design of the retractable sleeves is benefit to perform operation.

6 Claims, 10 Drawing Sheets (52) U.S. Cl.
CPC ......... *A61B 17/3474* (2013.01); *A61M 13/00*
(2013.01); *A61M 13/003* (2013.01); *A61B*
*17/0281* (2013.01); *A61B 17/3462* (2013.01);
*A61B 2017/3443* (2013.01); *A61B 2017/3464*
(2013.01); *A61B 2017/3486* (2013.01)

(58) Field of Classification Search
CPC . A61B 17/34; A61B 17/3433; A61B 17/3435;
A61B 2017/3443; A61B 2017/3447;
A61B 2017/3486; A61B 2017/3488;
A61M 2025/0175; A61M 2025/1061
See application file for complete search history.

(56) References Cited

U.S. PATENT DOCUMENTS

| | | | | |
|---|---|---|---|---|
| 5,957,888 | A | * | 9/1999 | Hinchliffe .......... A61B 17/3421 |
| | | | | 604/117 |
| 2005/0267463 | A1 | * | 12/2005 | Vanney .............. A61B 18/1492 |
| | | | | 606/41 |

* cited by examiner

TROCAR SET

CROSS-REFERENCE TO RELATED APPLICATION

This non-provisional application claims priority under 35 U.S.C. § 119(a) to Patent Application No. 105139683 filed in Taiwan, R.O.C. on Dec. 1, 2016, the entire contents of which are hereby incorporated by reference.

BACKGROUND

Technical Field

The instant disclosure relates to an instrument of minimally invasive surgery and, more particularly, to a trocar set.

Related Art

In modern surgery, a trocar, instead of a surgical knife, can be used to cut an opening on a human body for a doctor to perform an operation such as burning or cutting an internal tissue by medical instruments such as an optical fiber, an endoscope, or a laser. By way of the operations, wounds caused by the operation are smaller, pains patients feel are less, time for patients' lying in bed and rest after operations is shorter, and scars are smaller. Due to the small wounds and quick recoveries, the kind of operations is called minimally invasive surgery.

A trocar is a combination of a cutlery and a trocar set. The trocar set includes a long tube. The cutlery is fixed in the trocar set along the long tube. After the cutlery is used to cut an opening on a human body, the cutlery is removed from the long tube of the trocar set. Next, surgical instruments such as an optical fiber, an endoscope, or a laser can be inserted into the human body along the long tube to perform operations such as burning or cutting tissues.

During an operation stage, the length of the trocar set outside the human body is longer than that inside the human body. During either an instrument inserting stage or the operation stage, it is easily happened that the medical professionals have physical contact with the trocar set outside the human body. As a result of the trocar set being contacted, the wound may be enlarged, and patients may have greater pain intensity.

SUMMARY

To address the issue of prior art, the instant disclosure provides a trocar set. The length of the trocar outside the human body during an operation can be shortened, which is beneficial to perform the operation. The trocar set comprises a handle portion, a first sleeve, a second sleeve, and a gasbag. The handle portion comprises a grip, a connection part, and a first gas valve. The connection part extends from the grip and comprises an assembling channel. The first gas valve is connected to the connection part and communicates with the assembling channel The first sleeve comprises an assembling end and a sleeving end. The assembling end is assembled to the assembling channel and corresponding to the first gas valve. A sleeve wall of the sleeving end is provided with at least one first opening. The second sleeve is retractably connected to the sleeving end of the first sleeve. A sleeve wall of the second sleeve is provided with at least one second opening. The gasbag is connected to an end of the second sleeve away from the first sleeve and corresponds to the second opening. The second sleeve is capable of being retracted relative to the first sleeve such that the first sleeve can be received in the second sleeve, and the total length of the first sleeve and the second sleeve can be shortened.

In an embodiment, the first sleeve further comprises a first inner sleeve wall and a first outer sleeve wall. The first sleeve defines a first sleeve wall region and a second sleeve wall region. The first outer sleeve wall surrounds an exterior of the first inner sleeve wall in the first sleeve wall region. The first outer sleeve wall does not surround the exterior of the first inner sleeve wall in the second sleeve wall region. The first opening is disposed on the first outer sleeve wall.

Additionally, the second sleeve further comprises a second inner sleeve wall and a second outer sleeve wall. The second sleeve defines a third sleeve wall region and a fourth sleeve wall region. The second outer sleeve wall surrounds an exterior of the first outer sleeve wall in the third sleeve wall region. The second outer sleeve wall surrounds an exterior of the second inner sleeve wall in the fourth sleeve wall region. The first opening is disposed on the first outer sleeve wall, and the second opening is disposed on the second outer sleeve wall.

Additionally, a gas flow channel is formed between the first inner sleeve wall and the first outer sleeve wall, between the first opening, the first outer sleeve wall, and the second outer sleeve wall, and between the second outer sleeve wall and the second inner sleeve wall, and communicates with the second opening. After gas flows through the first gas valve, the gas flows along the gas flow channel and enters the gasbag through the second opening to have the gasbag inflated. The trocar set can be fixed to a human body by the gasbag.

In an embodiment, the trocar set further comprises a gas tight assembly. The gas tight assembly is disposed on a part of the first outer sleeve wall and the second outer sleeve wall and seals a portion where the first sleeve is connected to the second sleeve. In other words, the gas is restricted in the first sleeve and the second sleeve by the gas tight assembly to prevent a gas leak. Particularly, the gas inflated through the first gas valve can be restricted in the gas flow channel.

Additionally, the gas tight assembly further comprises a blocking component and a gas tight sleeve. The blocking component is assembled to the first sleeve and is adjacent to the sleeving end. The gas tight sleeve is connected to a portion where the first sleeve is connected to the second sleeve. The gas tight sleeve encloses the blocking component. As a result, the second sleeve moves away from the handle portion when the second sleeve is stretched, and a maximum stretching length is met when the second sleeve is stretched to contact the blocking component. It can be ensured that when the second sleeve is stretched, the gas won't leak based upon the gas tight ability of the gas tight sleeve.

Additionally, the trocar set further comprises a gas tight ring. The gas tight ring is connected to a part of the first sleeve and contacts a surface of the blocking component. The gas tight ring is enclosed by the gas tight sleeve to meet the gas tight ability.

Additionally, the gas tight assembly further comprises a fastening component. The fastening component is assembled to the sleeving end of the first sleeve and contacts an interior of the second sleeve. As a result, the first sleeve and the second sleeve are stably connected to each other and are hard to slide so as to prevent the first sleeve and the second sleeve from disengagement.

Additionally, when the second sleeve is retracted, the second sleeve moves towards the handle portion, the first sleeve is retracted in the second sleeve until the gas tight assembly contacts the connection part.

In an embodiment, the grip comprises an opening. The opening communicates with the assembling channel, the first sleeve, and the second sleeve. A cutlery or another surgical instrument can be put in the trocar set through the opening and can be further fixed in the first sleeve and the second sleeve.

In an embodiment, the trocar set further comprises a second gas valve. The second gas valve is connected to the connection part and communicates with the first sleeve. Specifically, the second gas valve provides greater amount of gas and has the gas flow into a human body to make a portion of an internal space of a human body inflated, which is beneficial of observing by an endoscope and performing an operation.

In another embodiment, a trocar set comprises a handle portion, a second sleeve, and a gas tight assembly. The handle portion comprises a grip, a connection part, and a second gas valve. The connection part extends from the grip and comprises an assembling channel. The second gas valve is connected to the connection part and communicates with the assembling channel. The first sleeve comprises an assembling end and a sleeving end. The assembling end is assembled to the assembling channel. The second sleeve is retractably connected to the sleeving end of the first sleeve such that the second gas valve, the assembling channel, the first sleeve, and the second sleeve communicate with one another. The second sleeve can be retracted relative to the first sleeve such that the first sleeve can be received in the second sleeve, and the total length of the first sleeve and the second sleeve can be shortened. The gas tight assembly further comprises a blocking component and a gas tight sleeve. The blocking component is assembled to the first sleeve and is adjacent to the sleeving end. The gas tight sleeve is connected to a portion where the first sleeve is connected to the second sleeve. The gas tight sleeve encloses the blocking component.

In yet another embodiment, a trocar set comprises a handle portion, a first sleeve, a second sleeve, a gas tight assembly, and a pulling band. The handle portion comprises a grip, a connection part, and a second gas valve. The connection part extends from the grip and comprises an assembling channel. The second gas valve is connected to the connection part and communicates with the assembling channel. The first sleeve comprises an assembling end and a sleeving end. The assembling end is assembled to the assembling channel The second sleeve is retractably connected to the sleeving end of the first sleeve such that the second gas valve, the assembling channel, the first sleeve, and the second sleeve communicate with one another. The second sleeve can be retracted relative to the first sleeve such that the first sleeve can be received in the second sleeve, and the total length of the first sleeve and the second sleeve can be shortened. The gas tight assembly comprises a fastening component and a gas tight sleeve. The fastening component is assembled to the sleeving end of the first sleeve and contacts an interior of the second sleeve. The gas tight sleeve is disposed on a part of the first sleeve and the second sleeve and seals a portion where the first sleeve is connected to the second sleeve. The pulling band crosses and is fixed to a portion connected to an exterior of the gas tight sleeve. The pulling band is adjacent to the fastening component.

According to embodiments of the trocar set of the instant disclosure, the trocar set is retractable by the connection of the first sleeve and the second sleeve. When a cutlery is removed, the length of the trocar set outside the humane body can be significantly shortened so as to avoid the trocar set outside the human body being contacted by the medical professionals. The trocar set outside the human body being contacted may make a wound enlarged. Consequently, it is benefit to medical professionals to perform operations.

DETAILED DESCRIPTION

Please refer to FIG. 1 to FIG. 4, which are respectively a stereoscopic diagram of a trocar set in a stretched state according to a first embodiment, an exploded view of the trocar set according to the first embodiment, a cross-sectional view of the trocar set in the stretched state according to the first embodiment, and a partial, cross-sectional view of the trocar set in the stretched state according to the first embodiment. As shown in FIG. 1 to FIG. 4, the trocar set 1 comprises a handle portion 10, a first sleeve 20, a second sleeve 30, a gasbag 40, and a gas tight assembly 50. The handle portion 10 comprises a grip 11, a connection part 13, a first gas valve 15, and a second gas valve 17. The grip 11 may be, but not limited to, a semicircular shell structure of which an interior is hollow. The connection part 13 extends from the grip 11 and is a column structure. The connection part 13 comprises an assembling channel 131. The assembly channel 131 is formed in a manner of penetrating through the connection part 13. The assembling channel 131 communicates with the interior of the grip 11. The first gas valve 15 and the second gas valve 17 may be assembled to the connection part 13. The first gas valve 15, the second gas valve 17, and the connection part 13 may be formed in one piece, alternatively. In addition, gas flow channels of the first gas valve 15 and the second gas valve 17 communicate with the assembling channel 131.

The first sleeve 20 comprises an assembling end 201 and a sleeving end 203. The assembling end 201 is assembled to the assembling channel 131 of the connection part 13. The first sleeve 20 extends from the assembling end 201 along a direction of a central axis of the assembling channel 131 and protrudes from the connection part 13. The first sleeve 20 may be a double layer sleeve which comprises a first inner sleeve wall 21 and a first outer sleeve wall 23. Specifically, the first sleeve 20 defines a first sleeve wall region 211 and a second sleeve wall region 213. The first outer sleeve wall 23 surrounds an exterior of the first inner sleeve wall 21 in the first sleeve wall region 211. The first outer sleeve wall 23 does not surround the exterior of the first inner sleeve wall 21 in the second sleeve wall region 213. The second sleeve wall region 213 is in the assembling channel 131 and corresponds to the first gas valve 15. In addition, the first outer sleeve wall 23 of the sleeving end 203 is provided with at least one first opening 231. In other words, gas introduced from the first gas valve 15 enters the first gas flow channel 25 through a region where the first outer sleeve wall 23 does not surround the first inner sleeve wall 21 and leaves the first gas flow channel 25 from the first opening 231.

The second sleeve 30 comprises a receiving end 32. The sleeving end 203 of the first sleeve 20 is inserted into the receiving end 32 of the second sleeve 30 such that the second sleeve 30 is retractably connected to an end of the first sleeve 20 away from the handle portion 10. The second sleeve 30 may be a double layer sleeve which comprises a second inner sleeve wall 31 and a second outer sleeve wall 33. The second sleeve 30 defines a third sleeve wall region 311, a fourth sleeve wall region 313, and a fifth sleeve wall region 315. The second outer sleeve wall 33, corresponding to the sleeving end 203, surrounds an exterior of the first outer sleeve wall 23 in the third sleeve wall region 311. The second outer sleeve wall 33 surrounds an exterior of the second inner sleeve wall 31 in the fourth sleeve wall region 313. The second outer sleeve wall 33 does not surround the second inner sleeve wall 31 in the fifth sleeve wall region 315. A second gas flow channel 35 is formed between the second outer sleeve wall 33 and the second inner sleeve wall 31. A region of the second outer sleeve wall 33 away from the sleeving end 203 is provided with at least one second opening 331. Specifically, an end of the second gas flow channel 35 corresponds to the first opening 231. Gas from the first gas valve 15 is introduced through the first opening 231 and enters the second gas flow channel 35, and then leaves the second gas flow channel 35 from the second opening 331.

The gasbag 40 is connected to an end of the second sleeve 30 away from the first sleeve 20. Particularly, the gasbag 40 is connected to a part of the second sleeve wall region 213 and connected to the third sleeve wall region 311. The air cell 40 corresponds to the second opening 331. In other words, the region where the first outer sleeve wall 23 does not surround the first inner sleeve wall 31, the first gas flow channel 25, the first opening 231, the second gas flow channel 35, and the second opening 331 communicate with one another to form a gas flow channel capable of inflating the gasbag 40. Gas introduced by the first gas valve 15 enters the gasbag 40 through the aforementioned gas flow channel to have the gasbag 40 inflated.

Figure 1:
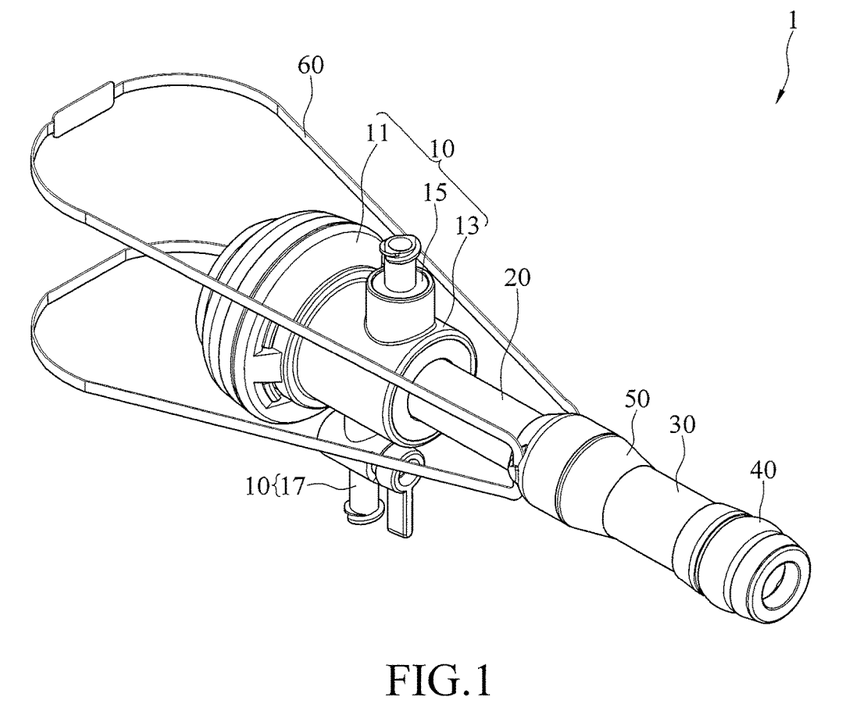
FIG. 1 illustrates a stereoscopic diagram of a trocar set in a stretched state according to a first embodiment.
Figure 2:
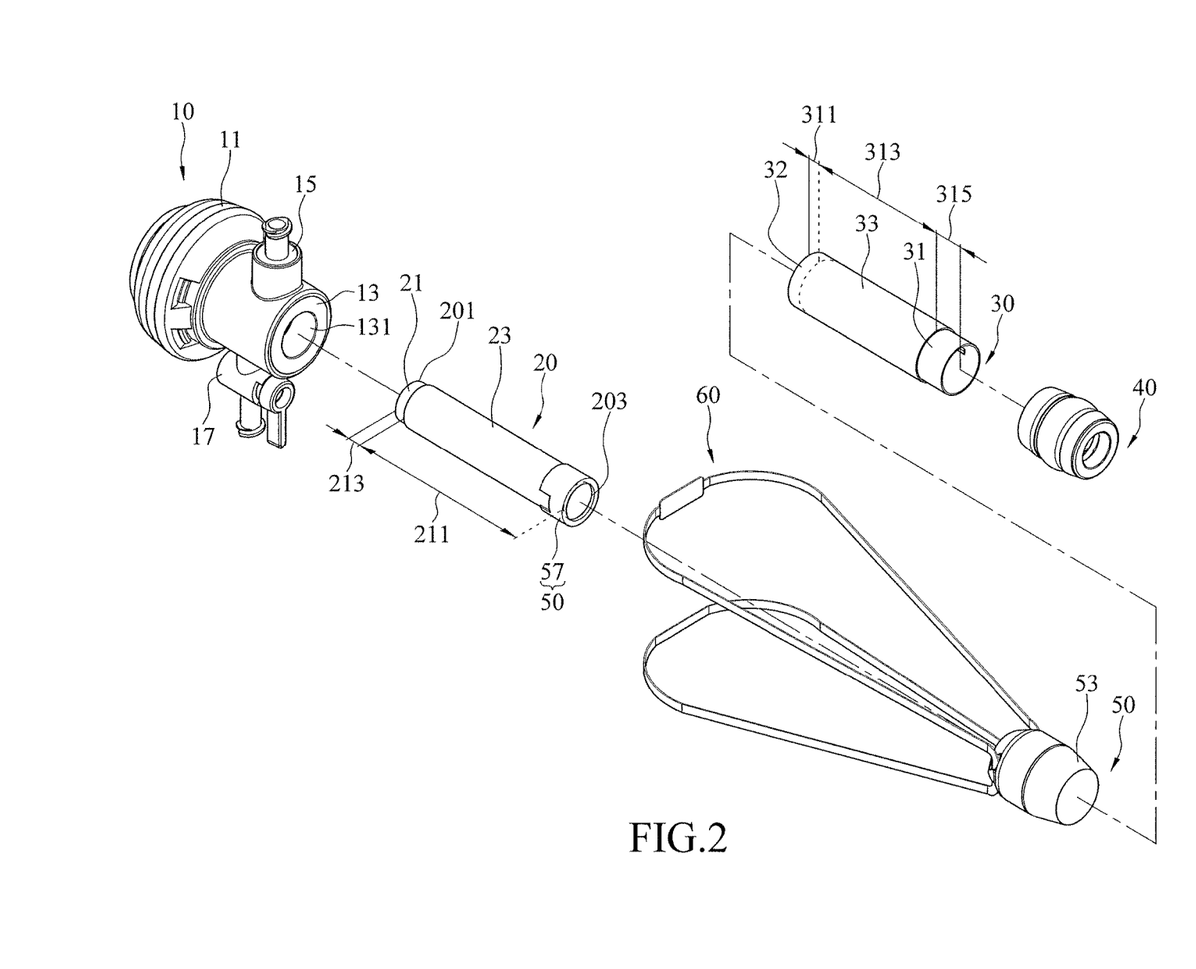
FIG. 2 illustrates an exploded view of the trocar set according to the first embodiment.
Figure 3:
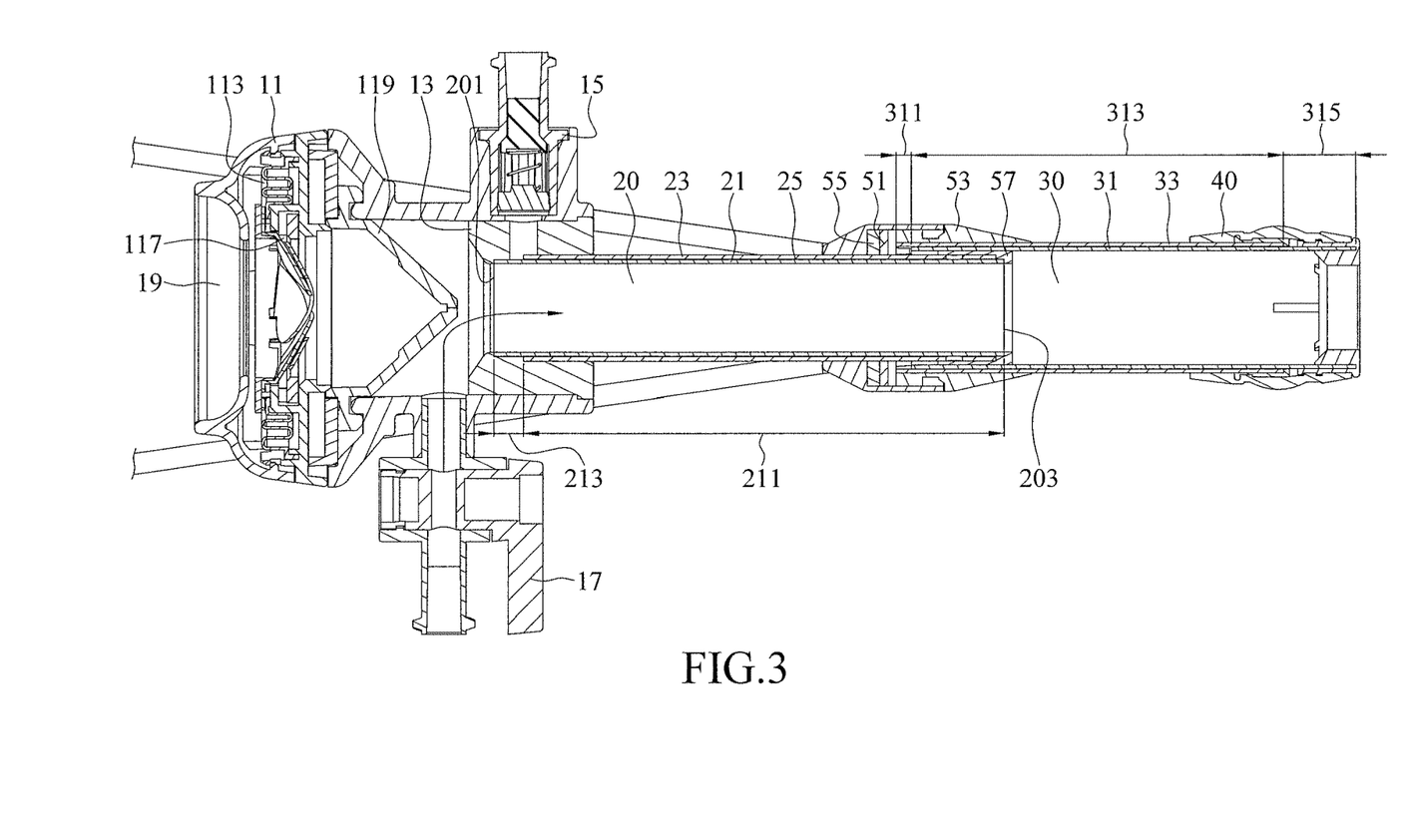
FIG. 3 illustrates a cross-sectional view of the trocar set in the stretched state according to the first embodiment.
Figure 4:
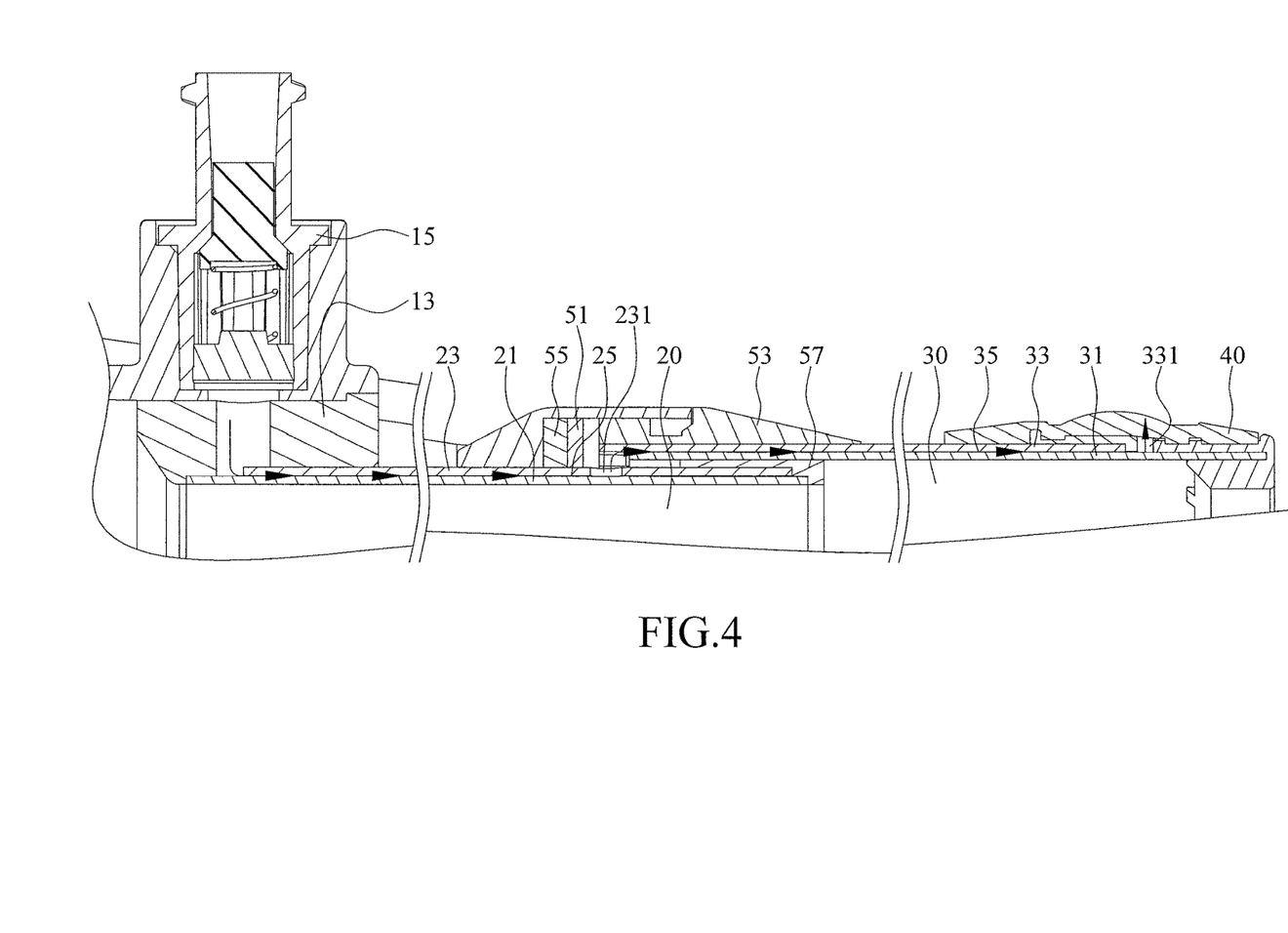
FIG. 4 illustrates a partial, cross-sectional view of the trocar set in the stretched state according to the first embodiment.
Figure 5:
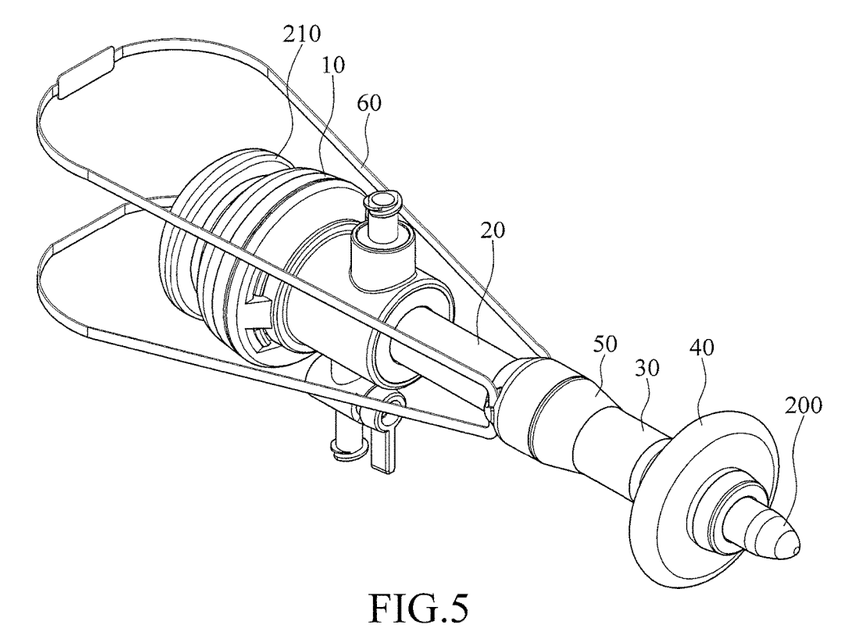
FIG. 5 illustrates a stereoscopic diagram of the trocar set in the stretched state in use according to the first embodiment.
Figure 6:
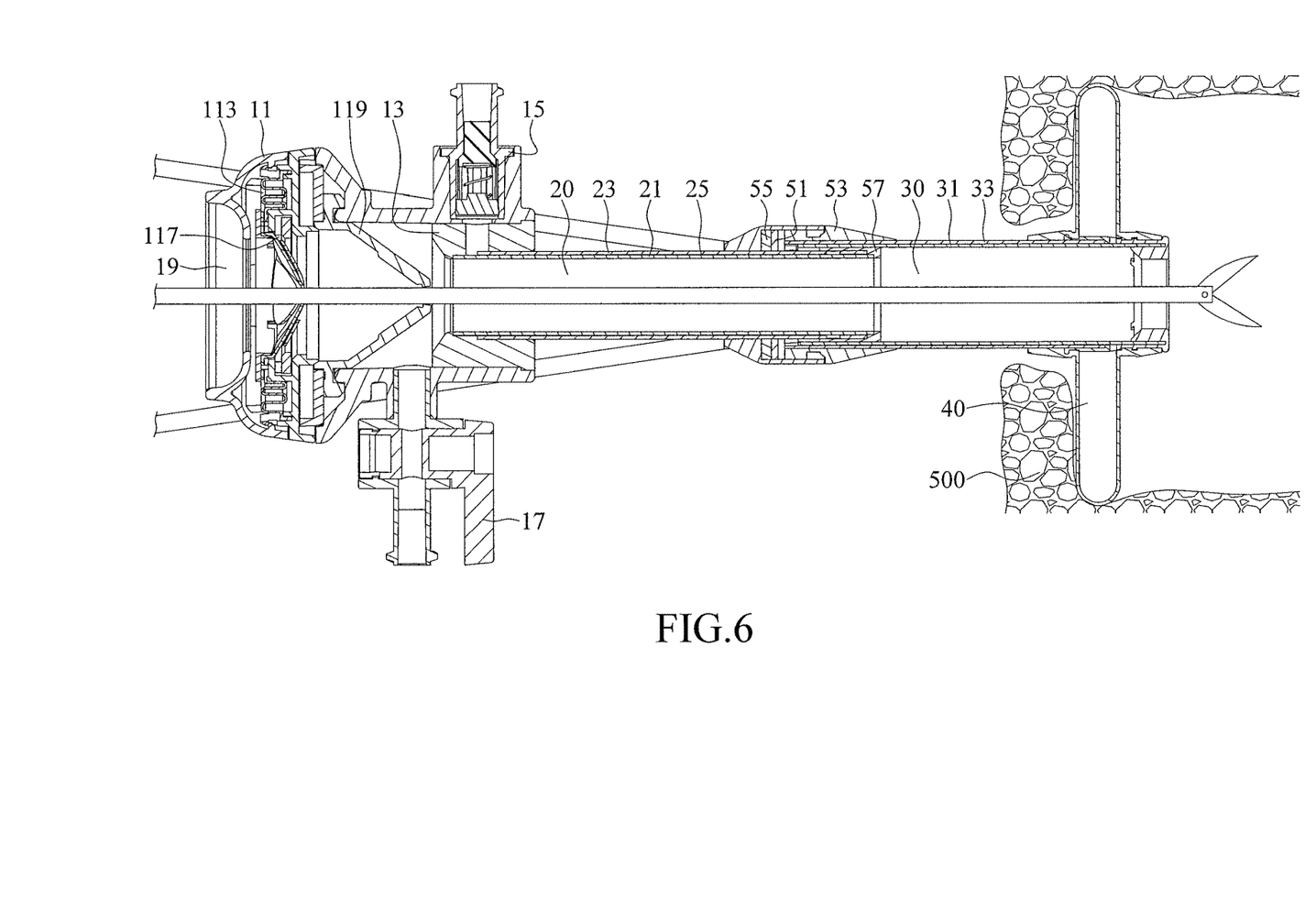
FIG. 6 illustrates a cross-sectional view of the trocar set in the stretched state according to the first embodiment.

Please refer to FIG. 5 and FIG. 6, which are respectively a stereoscopic diagram of the trocar set in the stretched state in use according to the first embodiment and a partial, cross-sectional view of the trocar set in the stretched state in use according to the first embodiment. As shown in FIG. 1 to FIG. 6, the trocar set 1 in practical use is installed with a cutlery 200. The cutlery 200 is inserted into an opening 19 in a rear end of the handle portion 10 and is installed to the grip 11, the connection part 13, the first sleeve 20, and the second sleeve 30. The cutlery 200 protrudes from the second sleeve 30 and is fixed to the handle portion 10 by a rear cover 210. Additionally, the grip 11 further comprises a first sealing component 117 and a second sealing component 119. The cutlery 200 being installed may be assembled to and contact the first sealing component 117 and the second sealing component 119. The first sealing component 117 and the second sealing component 119 can seal the gas flow channel such that the cutlery 200 having been fixed to the grip 11, the first sleeve 20, and the second sleeve 30 can prevent the gas from leaking to meet the gas tight ability.

As shown in FIG. 5 and FIG. 6, after the trocar set 1 in the stretched state is used to cut an opening on a human body 500, gas introduced from the first gas valve 15 may flow through the first gas flow channel 25, the first opening 231, the second gas flow channel 35, and the second opening 331 and then enter the gasbag 40. When the gasbag is inflated, the trocar set 1 can be fixed in the human body 500. Further, the first gas valve 15 may be a pressing type valve, which can inflate the gasbag 40 by pressing.

Figure 7:
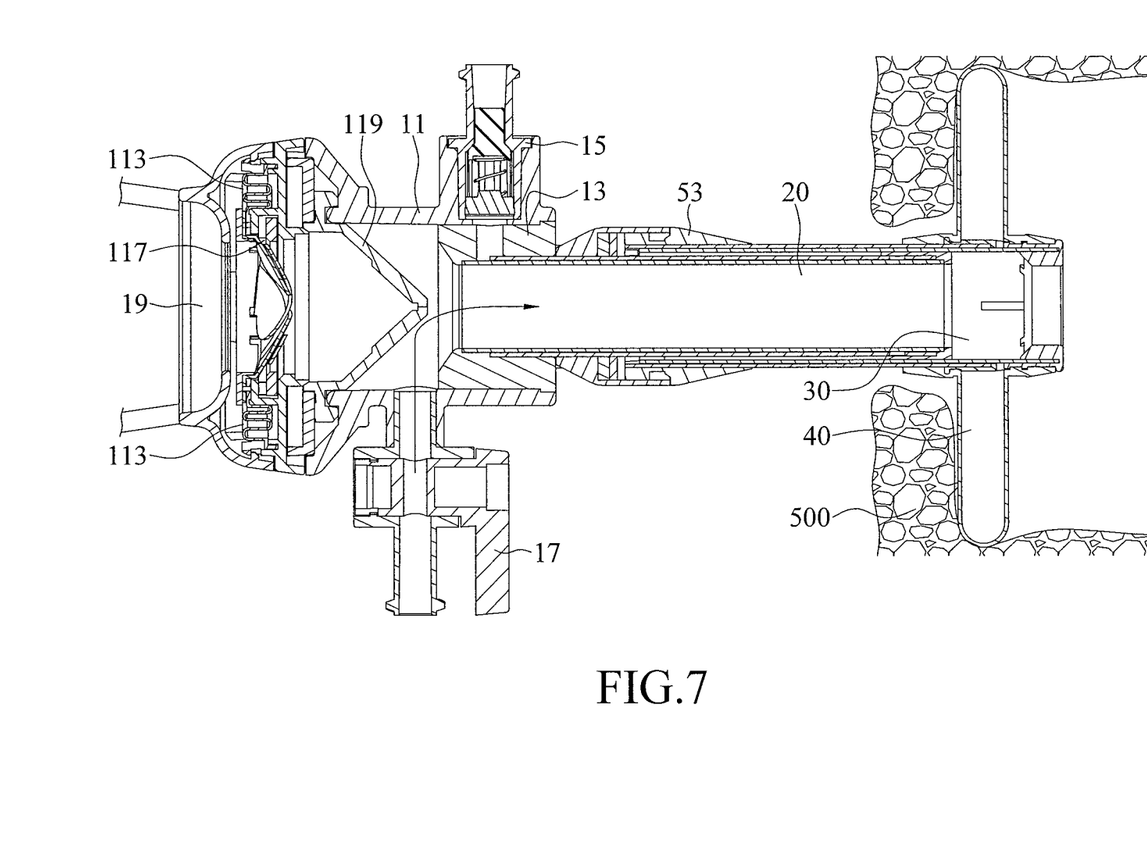
FIG. 7 illustrates a partial, cross-sectional view of the trocar set in a retracted state in use according to the first embodiment.
Figure 8:
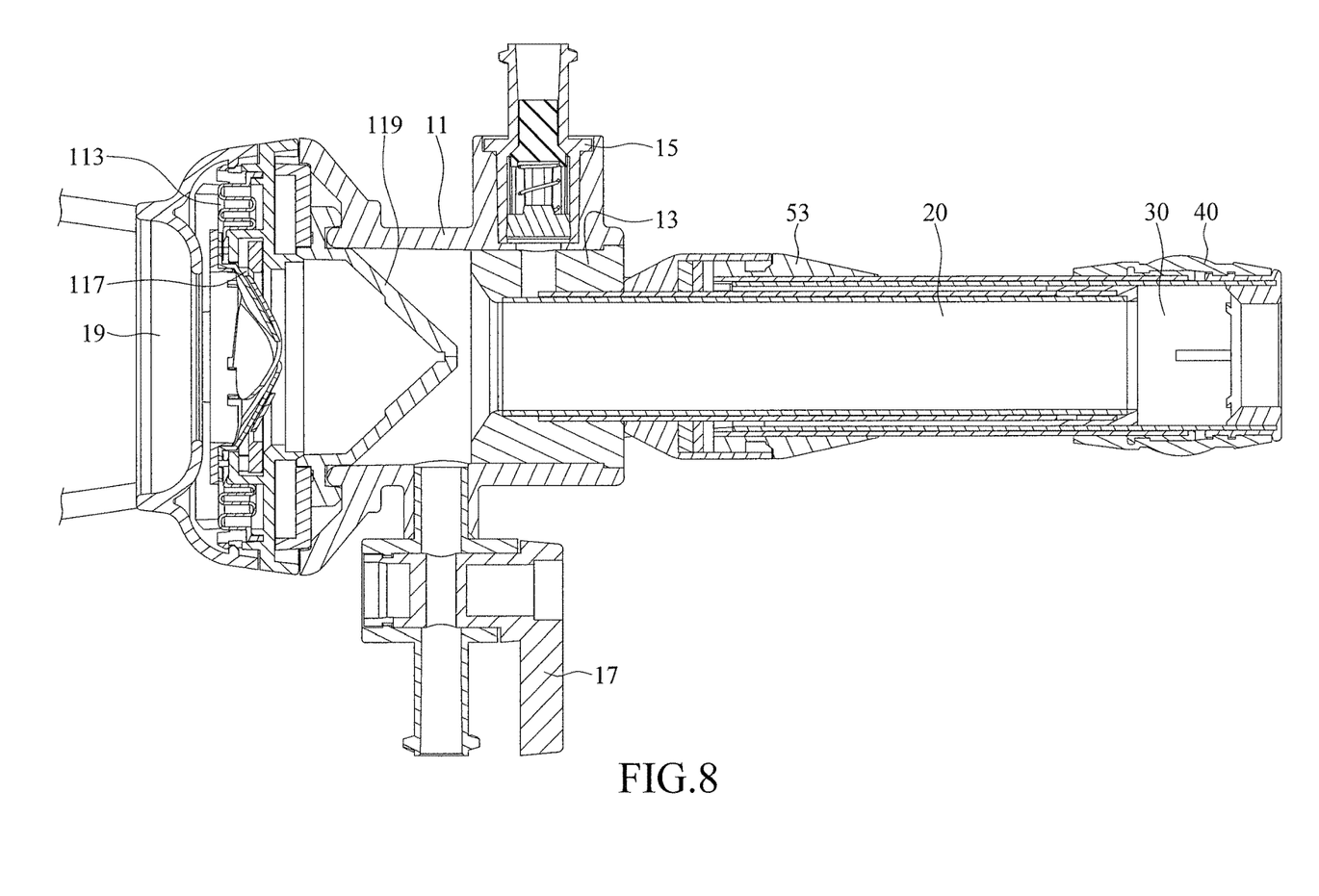
FIG. 8 illustrates a partial, cross-sectional view of the trocar set in the retracted state in use according to the first embodiment.
Figure 9:
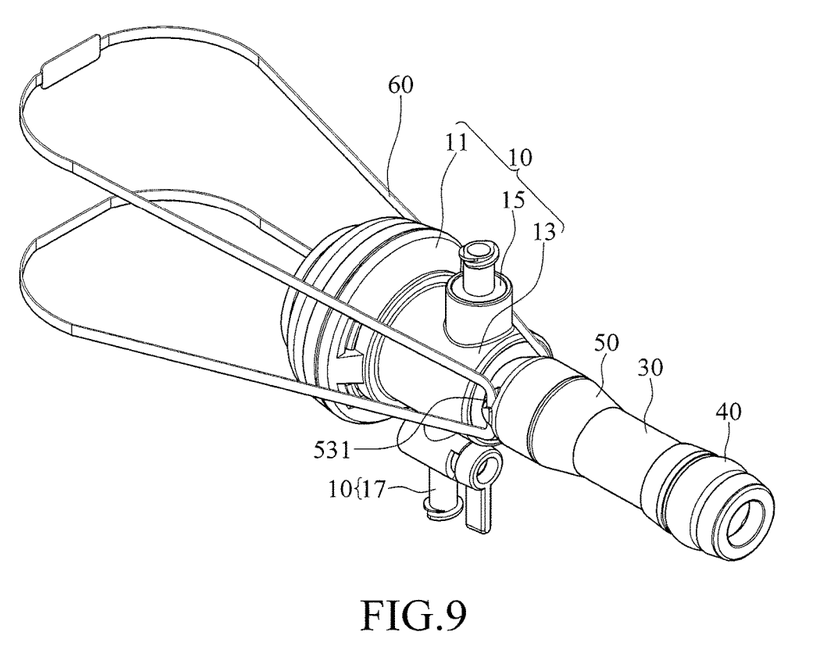
FIG. 9 illustrates a stereoscopic diagram of the trocar set in the retracted state according to the first embodiment.

Please refer to FIG. 7, FIG. 8, and FIG. 9, which are respectively a partial, cross-sectional view of the trocar set in a retracted state in use according to the first embodiment, a cross-sectional view of the trocar set in the retracted state according to the first embodiment, and a stereoscopic diagram of the trocar set in the retracted state according to the first embodiment. As shown in FIG. 7, the cutlery 200 can be removed from the trocar set 1 after the trocar set 1 is fixed to the human body 500 by the gasbag 40. The trocar set 1 can be pushed forward by the handle portion 10 to have the second sleeve 30 moved towards the handle portion 10 relative to the first sleeve 20, such that the first sleeve 20 can be retracted in the second sleeve 30 to be in the retracted state. Therefore, the length of the trocar set 1 outside of the human body 500 can be significantly shortened. Additionally, when the trocar set 1 is in the retracted stated, medical professionals may conveniently put medical instruments such as an endoscope, an optical fiber, or a laser into the human body along the first sleeve 20 and the second sleeve 30 and avoid contacting the trocar set 1. Additionally, the grip 11 comprises a butting block 113 capable of fixing medical instruments such as an endoscope, an optical fiber, or a laser.

Specifically, after the cutlery 200 is removed, gas can be inflated into the human body from the second gas valve 17 through the first sleeve 20 and the second sleeve 30 to have a human tissue expanded partially, which is beneficial of inserting medical instruments such as an endoscope, an optical fiber, or a laser, observing, and performing an operation. Specifically, the second gas valve 17 can be a switch of gas which may be connected to an external inflating device for inflation. Additionally, after an operation is accomplished, the first gas valve 15 can be turned on to have gasbag 40 deflated such that the trocar set 1 can be removed from the human body, as shown in FIG. 8, and FIG. 9.

As shown in FIG. 1 to FIG. 4., the gas tight assembly 50 of the trocar set 1 is disposed on a portion where the first sleeve 20 and the second sleeve 30 are connected to each other; therefore, the portion where the first sleeve 20 and the second sleeve 30 are connected to each other can be sealed to prevent a gas leak. Specifically, the gas tight assembly 50 further comprises a blocking component 51 and a gas tight sleeve 53. The blocking component 51 is assembled to an exterior of the first sleeve 20 and is adjacent to the sleeving end 203. The blocking component 51 is enclosed by the gas tight sleeve 53 to prevent the first sleeve 20 from being disengaged from the second sleeve 30. In an embodiment, the gas tight sleeve 53 is a two piece combination. Specifically, when the trocar set 1 is in the stretched state, the first opening 231 is between the second outer sleeve wall 33 and the blocking component 51.

Additionally, as shown in FIG. 7, FIG. 8, and FIG. 9, when the trocar set 1 is retracted, the second sleeve 30 moves towards the handle portion 10 relative to the first sleeve 20 until the gas tight assembly 50 contacts the connection part 13.

Additionally, the gas tight assembly 50 further comprises a gas tight ring 55 and a fastening component 57. The gas tight ring 55 is connected to the exterior of the first sleeve 20. In an embodiment, the gas tight sleeve 55 presses the gas tight ring 55 to have the gas tight ring 55 tightly attach to the first sleeve 20 to meet the gas tight ability. In an embodiment, the gas tight ring 53 contacts a surface of the blocking component 51 and is enclosed by the gas tight sleeve 53. As shown in the drawing, the gas tight ring 55 is, for example, on a surface of the blocking component 51 opposing the second outer sleeve wall 33. The gas tight ring 55 may also be disposed on a surface of the blocking component 51 facing the second outer sleeve wall 33. Alternatively, the gas tight ring(s) 55 may be disposed on both of the two surfaces of the blocking component 51. The fastening component 57 is disposed on the sleeving end 203 of the first sleeve 20. Particularly, the fastening component 57 encloses the sleeving end 203; therefore, the height of the sleeving end 203 is slightly greater than that of other regions of the first sleeve 20. The fastening component 57 contacts the second inner sleeve wall 31 of the second sleeve 30. Due to the fastening component 57, the second sleeve 30 may slide relative to the first sleeve 20 so as to stretch or to retract only when the second sleeve 30 is forced. As a result, the first sleeve 20 and the second sleeve 30 are steady after being stretched or retracted and are hard to slide so as to prevent the first sleeve 20 and the second sleeve 30 from disengagement.

Figure 10:
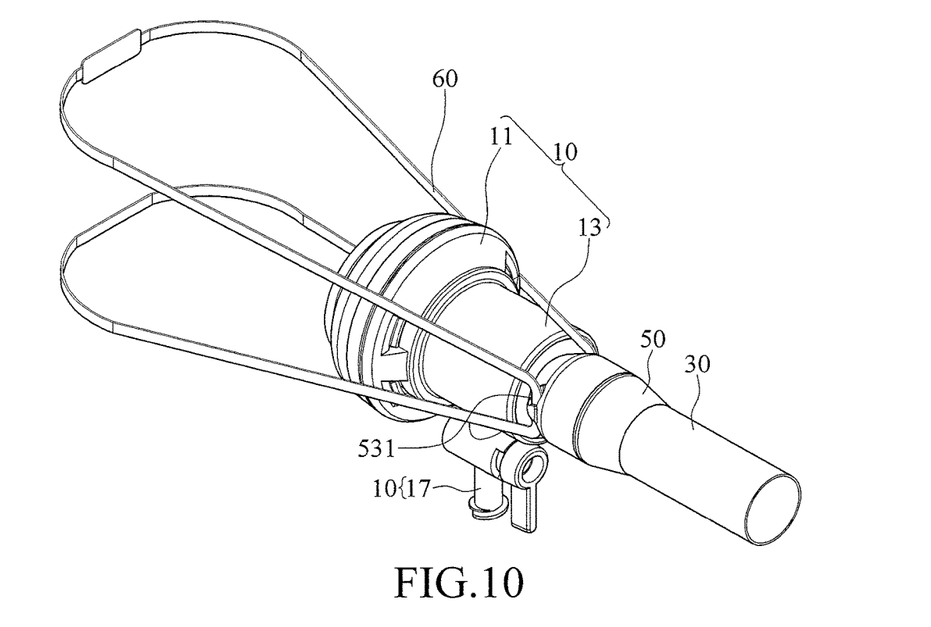
FIG. 10 illustrates a stereoscopic diagram of a trocar set in the retracted state according to a second embodiment.
Figure 11:
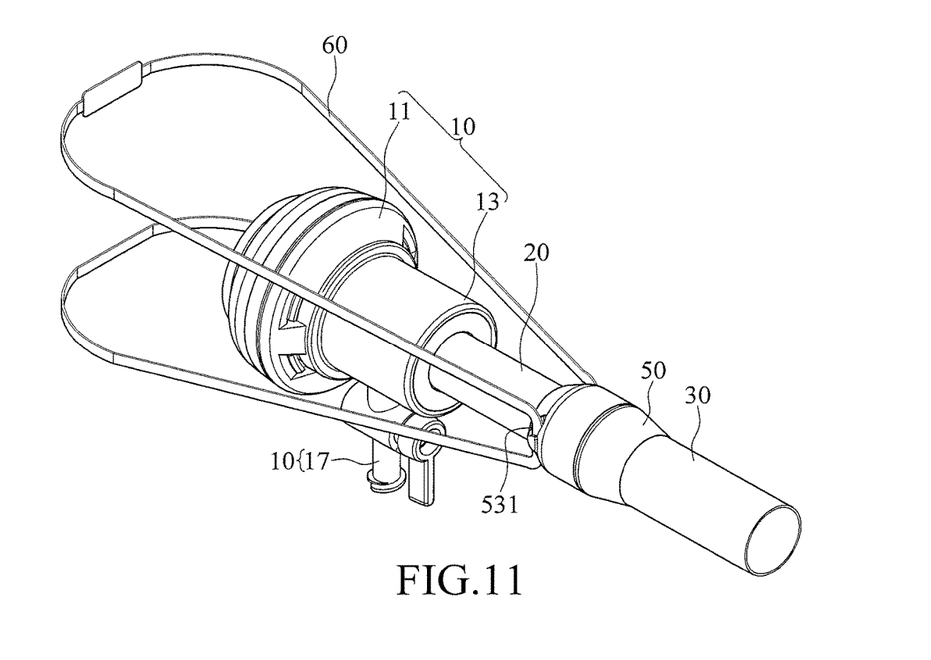
FIG. 11 illustrates a stereoscopic diagram of the trocar set in the stretched state according to the second embodiment.

Please refer to FIG. 10 and FIG. 11, which are stereoscopic diagrams of a trocar set in the retracted state and in the stretched state respectively according to a second embodiment. As shown in FIG. 10 and FIG. 11, a difference between the first embodiment and the second embodiment is that the trocar set 1 does not have the gasbag 40 and the first gas valve 15. Although the trocar set 1 cannot be fixed to a human body by the gasbag, the trocar set 1 can be stably set by a stand or other measures after penetrating and allow instruments to be inserted there through. In order to prevent a gas leak, it is merely required that the gas tight assembly 50 is connected to a portion where the first sleeve 20 and the second sleeve 30 are connected to each other. As a result, there may be no need of the structure of the double layer sleeve, and, consequently, the cost may be lower. The gas tight assembly 50 may comprise the blocking component 51 and the gas tight sleeve 53 and may further comprise the gas tight ring 55 and the fastening component 57.

Additionally, as shown in FIG. 1, FIG. 5, FIG. 9, and FIG. 11, the trocar set 1 further comprises at least one pulling band 60. The pulling band 60 is at an exterior of the gas tight assembly 50 and is adjacent to the fastening component 57. An outer wall of the gas tight sleeve 53 is provided with two crossing channels 531, which do not penetrate through the gas tight sleeve 53. The pulling band 60 crosses the crossing channels 531 to form a closed loop structure. When the first sleeve 20 is forced to be retracted in the second sleeve 30, and the pulling band 60 is accordingly forced towards outside, an inward force and an outward force can be balanced and then the position of the second sleeve 30 can be stably fixed. In an embodiment, a pulling band set comprising two pulling bands symmetric to each other may be adopted. For example, the pulling band 60 may be, but not limited to, fixed to the connection part 13. In a state as shown in FIG. 5, the pulling band 60 can be pulled after the gasbag 40 is inflated to make sure that the trocar set 1 is fixed to a human body. Or, the pulling band 60 may be pulled after the surgery to assist in removing the trocar set 1 from the human body. Additionally, in the first embodiment, the gasbag has to be deflated in advance such that the trocar set can be removed by the pulling band 60 after a surgery.

According to embodiments of the trocar set of the instant disclosure, the trocar set is retractable by the connection of the first sleeve and the second sleeve. When the cutlery is removed from the trocar set, the first sleeve can be retracted in the second sleeve; therefore, the length of the trocar set outside of a humane body can be significantly shortened so as to avoid the trocar set being unintentionally contacted by medical professionals. A trocar set outside of the humane body being contacted may cause pain and make a wound enlarged. Consequently, it is benefit to medical professionals to insert instruments and perform operations.

While the instant disclosure has been described by way of example and in terms of the preferred embodiments, it is to be understood that the instant disclosure needs not be limited to the disclosed embodiments. For anyone skilled in the art, various modifications and improvements within the spirit of the instant disclosure are covered under the scope of the instant disclosure. The covered scope of the instant disclosure is based on the appended claims.

What is claimed is:

1. A trocar set, comprising:
   a handle portion comprising a grip, a connection part, and a first gas valve, wherein the connection part extends from the grip and comprises an assembling channel, and the first gas valve is connected to the connection part and communicates with the assembling channel;
   a first sleeve comprising an assembling end, a sleeving end, a first gas flow channel, a first inner sleeve wall and a first outer sleeve wall, wherein the assembling end is assembled to the assembling channel and is disposed corresponding to the first gas valve, a sleeve wall of the sleeving end is provided with at least one first opening, the first sleeve defines a first sleeve wall region and a second sleeve wall region, the first outer sleeve wall surrounds an exterior of the first inner sleeve wall in the first sleeve wall region, the first outer sleeve wall does not surround the exterior of the first inner sleeve wall in the second sleeve wall region, and the first opening is disposed on the first outer sleeve wall;
   a second sleeve comprising a second gas flow channel, wherein the second sleeve is retractably connected to the sleeving end of the first sleeve, and a sleeve wall of the second sleeve is provided with at least one second opening; and
   a gasbag connected to an end of the second sleeve away from the first sleeve and corresponding to the second opening;
   wherein the gasbag is capable of being inflated through the first gas flow channel, the first opening, the second gas flow channel, and the second opening.

2. The trocar set of claim 1, wherein the first gas flow channel is formed between the first inner sleeve wall and the first outer sleeve wall.

3. The trocar set of claim 1, wherein the second sleeve further comprises a second inner sleeve wall and a second outer sleeve wall, the second sleeve defines a third sleeve wall region and a fourth sleeve wall region, the second outer sleeve wall surrounds an exterior of the first outer sleeve wall in the third sleeve wall region, the second outer sleeve wall surrounds an exterior of the second inner sleeve wall in the fourth sleeve wall region, and the second opening is disposed on the second outer sleeve wall.

4. The trocar set of claim 3, wherein the second gas flow channel is formed between the second inner sleeve wall and the second outer sleeve wall.

5. The trocar set of claim 1, further comprising a second gas valve, the second gas valve being connected to the connection part and communicating with the first sleeve.

6. The trocar set of claim 1, wherein the grip comprises an opening, the opening communicates with the assembling channel, the first sleeve, and the second sleeve.

* * * * *